US006464838B1

(12) United States Patent
Charrin et al.

(10) Patent No.: US 6,464,838 B1
(45) Date of Patent: Oct. 15, 2002

(54) PROCESS FOR THE RECOVERY OF COMPOUNDS PRESENT IN THE HEAVY PRODUCTS AFTER THEIR PREPARATION

(75) Inventors: Jean-Jacques Charrin, Lyons (FR); Francoise Igersheim, Lyons (FR); Antonio Queiroz, Sao Paulo (BR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/350,909

(22) Filed: Jul. 12, 1999

(30) Foreign Application Priority Data

Jul. 10, 1998 (FR) .............................. 98 08935

(51) Int. Cl.$^7$ .......................... B01D 3/34; C07C 37/74; C07C 37/86; C07C 39/04
(52) U.S. Cl. ............................ 203/29; 203/20; 203/34; 203/35; 203/DIG. 6; 203/DIG. 25; 568/716; 568/724
(58) Field of Search .................. 203/28–29, 34, 203/35, DIG. 6, 6, DIG. 25, 100, 50, 91, 20, 36, 37; 568/724, 716

(56) References Cited

U.S. PATENT DOCUMENTS 3,764,583 A * 10/1973 Newton et al. ............. 528/174
3,833,943 A * 9/1974 Sturtevant .................. 210/152
4,365,081 A * 12/1982 Shimizu et al. ............... 203/6
5,221,440 A * 6/1993 Miyagi et al. ................ 203/37
5,446,196 A * 8/1995 Benedix et al. ............. 560/352
5,734,075 A * 3/1998 Fauconet et al. ........... 560/218

FOREIGN PATENT DOCUMENTS

| EP | 0 286 408 | * 12/1988 |
| JP | 5573795 | * 6/1980 |
| JP | 5573796 | * 6/1980 |

OTHER PUBLICATIONS

Roget's "International Thesaurus" 3rd ed. Crowell Co., 1834.*
Webster's II, "New Riverside University Dictionary".*
Al–Soufi et al Thermal Cracking (Soaker–Visbreaking) Studies on Qaiyarah Long Residues).*

* cited by examiner

Primary Examiner—Virginia Manoharan
(74) Attorney, Agent, or Firm—Burns, Doane, Swecker & Mathis, L.L.P.

(57) ABSTRACT

A process for the recovery of compounds present in a mixture containing residues of heavy products is provided. The process includes conducting a reaction and distillation to obtain the compounds and residues and macerating the residues before they can set to mass. The residues can then be destroyed. The process is particularly suitable for the treatment of the residues obtained in the preparation of phenol from cumene.

15 Claims, No Drawings

PROCESS FOR THE RECOVERY OF COMPOUNDS PRESENT IN THE HEAVY PRODUCTS AFTER THEIR PREPARATION

This application claims priority under 35 U.S.C. §§ 119 and/or 365 to Patent Application No. 98-08935 filed in France on Jul. 10, 1998; the entire content of which is hereby incorporated by reference.

The present invention relates to a process for the recovery of compounds present in a mixture of heavy products, the said mixture of heavy products arising from a process for preparing one of the compounds which it is desired to recover.

It has always been one of the essential concerns in industrial processes to restrict as far as possible the wastage of products (reactants/final products), either for the obvious reasons of process economics, but also for reasons connected with the environment and in order to avoid an excessive multiplication of the treatments of effluents or residual products.

This problem is the more serious if the process leads to the formation of viscous heavy products in which non-negligible quantities of desired or potentially valuable products are trapped.

This is especially the case in the preparation of phenol from cumene. It must be stated that, within the meaning of the invention, heavy products are understood as products having a high boiling point. In the particular case of the reaction indicated above, these heavy products contain mainly cumylphenols and dimers of α-methylstyrene.

The most common process for treating heavy products coming from the preparation of phenol comprises carrying out a thermal cracking operation on these residues. In more detail, this means carrying out a reaction during which the molecules are dissociated into desired or potentially valuable products, followed by an immediate distillation of the products obtained in the dissociation. The disadvantage of this process is the fact that the relatively high temperatures applied (about 320° C.) are the cause of the appearance of impurities, such as the cresols, which are difficult to separate and which consequently will contaminate the recovered compounds.

It has therefore been suggested to employ an acid catalyst, such as phosphoric acid, sulphuric acid or organic sulphonic acids. The use of the catalyst allows the temperature of the reaction to be lowered and hence avoids the appearance of contaminating impurities. However, this catalytic process has the disadvantage of making it difficult to exploit the value of the residues obtained. On the one hand, it has been found that these residues, apart from their high viscosity, contain dispersed solids coming from the presence of the catalyst, and sodium salts, which contributes to making their handling extremely complex, if not impossible. On the other hand, and this constitutes a major disadvantage, these solid residues can very easily and quickly set to a mass, which makes the apparatus unusable at least for some time. This is because, in the case of setting to a mass, it is necessary to clean out of the apparatus the solidified residues by employing powerful mechanical cleaning means.

As is easy to see, at the present time there are no processes available which allow compounds contained in a mixture of heavy products to be recovered in the best way, while at the same time making it possible, easy and profitable to exploit the value of the residues obtained (essentially destruction with heat recovery).

These objects and others are achieved by the present invention which relates to a process for the recovery of compounds contained in a mixture of heavy products, wherein a reaction/distillation is carried out, by means of which, on the one hand, the said compounds and, on the other hand, residues are obtained; the process according to the invention comprising carrying out dilaceration or masceration of the residues, before their destruction and before they set to a mass.

In effect, it has been found that an operation of disintegrating the residues obtained after the reaction/distillation avoided the setting to a mass in the apparatus or at least allowed the onset of this phenomenon to be delayed sufficiently for the residues to be transported to a boiler or any other apparatus in which they are burned.

Moreover, the process according to the invention permits the recovery of significant quantities of compounds present in the mixture of heavy products.

However, other advantages and characteristics of the present invention will appear more clearly when reading the description and the examples which follow.

Thus, the process according to the invention involves the recovery of compounds contained in a mixture of heavy product.

First of all, the mixture of heavy products forms part of the products synthesized in the course of the main reaction.

Taking the example of the preparation of phenol from cumene (main reaction) comprising the decomposition of the intermediate cumyl hydroperoxide, products such as α-methylstyrene (potentially valuable) as well as other products having a boiling point higher than that of phenol are formed besides the phenol and acetone. In particular, the cumylphenols and also dimers of α-methylstyrene appear among such products.

It is this mixture containing the cumylphenols and also the dimers of α-methylstyrene which is termed the mixture of heavy products in the particular case of this reaction. Moreover, it should be noted that this mixture is alkaline as the result of preceding treatments.

The mixture directly obtained after the reaction of decomposing the cumyl hydroperoxide is in the usual way treated in order, in the main, to separate the phenol and the acetone. In general, this is done by carrying out at least one distillation stage.

The mixture of heavy product according to the present invention corresponds to that obtained after having carried out the above mentioned separation stage.

The further operation of reaction/ distillation (or cracking) according to the process of the invention can be carried out with or without a catalyst. Preferably, the reaction is carried out with a catalyst.

Generally, the employed catalyst is a catalyst of the mineral acid or organic acid type. Sulphuric acid is an appropriate example of a mineral acid which can be used as such a catalyst. Examples of organic acids, which may be mentioned include, in particular, the organic sulphonic acids and preferably para-toluenesulphonic acid.

According to a preferred embodiment of the invention, the reaction/distillation of the mixture of heavy products is carried out in the presence of an organic acid and especially para-toluenesulphonic acid.

The quantity of catalyst used can be determined without difficulty by a person skilled in the art. To illustrate this, the quantity of catalyst used is such that the concentration of acid, after the neutralization of the base present in the mixture of heavy products to be treated, is more particularly 0.1 to 3% by weight of the flow of mixture to be treated.

In an advantageous manner, the catalyst is brought into contact upstream of the apparatus in which the treatment of the mixture of heavy products is carried out.

Moreover, and according to a particular embodiment of the process of the invention, the mixture of heavy products is, after having been brought into contact with the catalyst, at first homogenized.

To do this, any type of classic mixer in this field is used. Preferably, this homogenization is carried out in a static mixer.

The operation of treating the mixture of heavy products thus consists of a reaction/ distillation.

The latter is carried out in a reactor advantageously fitted with stirring means.

Moreover, a distillation column is mounted above this reactor.

Depending on the products to be separated, this column has a number of theoretical plates of between 3 and 10, preferably between 4 and 6.

The column can contain stacked packing, rings or trays (perforated, valve trays, bubble cap trays, etc.).

The process according to the invention is carried out under such conditions that the reaction temperature remains between 200 and 300° C., preferably between 220 and 260° C. These temperatures apply at atmospheric pressure.

It is quite clear that it would not be a deviation from the scope of the present invention to carry out this operation under a reduced pressure or even under a slight overpressure, in which case the temperature would consequently be adapted.

The potentially valuable compounds are recovered at the top of the distillation column.

The process according to the invention thus allows recovery of not only the phenol by cracking the cumylphenols present in the mixture of heavy products but also α-methylstyrene by cracking the cumylphenols and by cracking the dimer of α-methylstyrene.

After condensing the said compounds, a part is recycled to the column for constituting the reflux, and the remainder is separated for storage or subjected to further treatments for separating the diverse constituents.

In a very advantageous manner, pure compounds are recovered. Thus, the phenol recovered according to the process of the invention is essentially free of cresols.

A variant of the present invention comprises, once the compounds have been recovered, adding a base in order to neutralize the residual acidity due to the use of the catalyst. The justification for this is that it has been found that the presence of species such as $SO_3$ and/or $SO_2$ can cause a loss of recovered compounds owing to condensation reactions which are the converse of the reactions carried out during the reaction/distillation stage.

In order to avoid or to limit as far as possible any significant production of foam, it can be advantageous to introduce at least one antifoaming agent into the apparatus where the reaction/ distillation of the heavy products is carried out.

In particular, antifoaming agents based on silicones are used, which are resistant under the conditions of carrying out the reaction/distillation, such as the products from the Rhodorsil® (commercially available from Rhodia Chimie) range.

This antifoaming agent is preferably introduced directly into the apparatus where the residues are treated.

The quantity varies within wide limits and can be defined without difficulty by a person skilled in the art.

As has been indicated above, the process according to the invention comprises especially the dilaceration of the residues which have undergone the reaction/distillation operation which has just been described.

In particular, the residues are disintegrated at the outlet from the reaction/distillation.

In detail, if the process according to the invention is applied discontinuously, the dilaceration operation is then carried out immediately following the reaction/distillation.

In the case where the process according to the invention is carried out continuously, the dilaceration operation is carried out directly on the residues without intermediate storage, as soon as they are withdrawn from the apparatus in which the reaction/ distillation has taken place. This makes it possible to avoid any intervening setting to a mass of the said mixture of compounds.

It must be stated that the feed rate of the mixture of heavy products and the sum of the rates of compounds and residues taken off are adapted in such a way that an installation is obtained whose functioning is continuously stable.

A further advantage of the present invention is that it is entirely suitable for a continuous treatment.

The operation of dilaceration according to the invention is carried out by means of an apparatus decreasing the size of particles in suspension, homogenizing and conveying said particles. The dilacerator or mascerator pumps are particularly suitable to the invention. These pumps are well known to the one skilled in the art. They are sold for example by the following companies: Moritz, Mouvex, and Baudot-Hardol.

As an illustration, the dilacerator pumps may comprise a rotor generally tilted with respect to the rotation axis, said rotor preferably having grinding means (such as cogs, for example). As for the stator, it usually comprises slotted rings."

The residues are thus taken off from the reactor, in which the reaction/distillation has taken place, in order to be fed to a vessel fitted with such a pump.

It would not be a deviation from the scope of the present invention to add to the residues, before the dilaceration operation, a mixture whose boiling point is higher than the boiling temperature of the residues. For example, it can be advantageous to add the compounds of high boiling point, resulting from the preparation of cumene.

The residues coming out of the process according to the invention, if appropriate with the addition of a mixture having a high boiling point, are therefore disintegrated in this way before they are destroyed by combustion with recovery of heat.

It is to be noted that, for reasons of the corrosivity of these residues, it is advantageous to neutralize these latter after the dilaceration operation, by adding a base thereto. For example, alkali metal hydroxides can be used.

It should also be stated that it is quite conceivable to add basic compounds destined to be destroyed later, if these are present on the industrial site. Quite clearly, this is possible to the extent that these basic compounds do not react with the residues to give insoluble products liable to cause operational problems (blockage).

In an obvious manner, the materials employed for the apparatus are selected in such a way that they can resist the corrosivity of the residues treated, the more so if a catalyst is employed for effecting the reaction/distillation stage.

Concrete examples will now be given.

EXAMPLE 1) 750 kg/h of residues of the following composition:

about 40% of cumylphenols, about 20% of dimers of α-methylstyrene, about 2% of phenol, other heavy products to make up 100%, are fed to a static mixer.

At the same time, 15 kg/h of para-toluenesulphonic acid (65% aqueous solution) are added.

2) The resulting mixture is introduced into a reactor fitted with stirring means and heated to a temperature of 250° C. Above the reactor, a distillation column with 8 bubble cap trays is mounted. The reflux rate is 50%. The residence time of the residues in the reactor is about 3 hours.

3) At the top of the distillation column, a flow of 375 kg/h is recovered, comprising:

about 33% of phenol, about 40% of α-methylstyrene, about 15% of cumene, diverse, not determined products to make 100%.

Sodium hydroxide for neutralizing the residual acidity is added to the flow of these compounds.

4) 375 kg/h of residues are taken off from the reactor and mixed with 200 kg/h of a mixture of compounds whose boiling point is above 250° C. and which come from the preparation of cumene.

This mixture is dilacerated by means of a Moritz® type pump (dilacerator pump) and ultimately incinerated without intermediate storage.

COMPARISON EXAMPLE

The same experiment is carried out with replacement of the dilacerator pump by a conventional centrifugal pump.

A blockage of the incineration feed line is soon observed.

What is claimed is:

1. A process for the recovery of compounds contained in a mixture of heavy products, comprising steps of:

conducting a reaction and a distillation to obtain said compounds and residues;

mascerating/dilacerating the residues by decreasing the size of particles in the residues, homogenizing and conveying the particles before the residues set to mass; and destroying the residues.

2. A process according to claim 1, wherein the masceration/dilaceration step is carried out at the outlet of a distillation apparatus.

3. A process according to claim 1, wherein the masceration/dilaceration step is carried out by means of a mascerator/dilacerator pump.

4. A process according to claim 1, wherein the heavy products come from the manufacture of phenol.

5. A process according to claim 4, wherein the phenol is obtained from cumene.

6. A process according to claim 1, wherein the residues are, before the masceration/dilaceration step, brought into contact with a mixture whose boiling point is higher than the boiling point of the residues.

7. A process according to claim 6, wherein the mixture is a byproduct resulting from the preparation of cumene.

8. A process according to claim 1, wherein the reaction and distillation is carried out in the presence of a catalyst.

9. A process according to claim 8, wherein the catalyst is selected from the group consisting of sulphuric acid and organic sulphonic acids.

10. A process according to claim 1, wherein the residues are neutralized after the masceration/dilaceration step, before they are destroyed.

11. A process according to claim 1, wherein the reaction and distillation is carried out in the presence of an antifoaming agent.

12. A process according to claim 11, wherein the antifoaming agent is a silicone.

13. A process according to claim 1, wherein the reaction and distillation are carried out at a temperature between 200 and 300° C.

14. A process according to claim 13, wherein the reaction and distillation are carried out at a temperature between 220 and 260° C.

15. A process according to claim 1, wherein the compounds are neutralized.

* * * * *